(12) United States Patent
Umar (10) Patent No.: US 9,987,038 B2
(45) Date of Patent: Jun. 5, 2018

(54) FOLLICLE PUNCH FOR USE WITH CURLED FOLLICLES (71) Applicant: Sanusi Umar, Redondo Beach, CA (US)

(72) Inventor: Sanusi Umar, Redondo Beach, CA (US)

(*) Notice: Subject to any disclaimer, the term of this patent is extended or adjusted under 35 U.S.C. 154(b) by 348 days.

(21) Appl. No.: 14/387,984

(22) PCT Filed: Nov. 26, 2013

(86) PCT No.: PCT/US2013/071991
§ 371 (c)(1),
(2) Date: Sep. 25, 2014

(87) PCT Pub. No.: WO2014/082077
PCT Pub. Date: May 30, 2014

(65) Prior Publication Data
US 2015/0250493 A1 Sep. 10, 2015

Related U.S. Application Data (60) Provisional application No. 61/874,664, filed on Sep. 6, 2013, provisional application No. 61/729,733, filed on Nov. 26, 2012.

(51) Int. Cl.
A61B 17/50 (2006.01)
A61B 17/3205 (2006.01)
(Continued)

(52) U.S. Cl.
CPC .... A61B 17/32053 (2013.01); A61B 17/3468 (2013.01); A61B 2017/00752 (2013.01);
(Continued)

(58) Field of Classification Search
CPC ...... A61B 17/32053; A61B 17/320068; A61B 17/3468; A61B 2017/00752;
(Continued)

(56) References Cited

U.S. PATENT DOCUMENTS

2007/0156164 A1* 7/2007 Cole ................ A61B 17/32053
606/187
2008/0234698 A1* 9/2008 Oostman ............ A61B 10/0266
606/133
2011/0160746 A1* 6/2011 Umar ............... A61B 17/32053
606/133

OTHER PUBLICATIONS

International Preliminary Report on Patentability dated Nov. 17, 2015.
(Continued)

Primary Examiner — Elizabeth Houston
Assistant Examiner — Mohammed Gabr
(74) Attorney, Agent, or Firm — Law Office of Michael O'Brien (57) ABSTRACT A punch that is particularly useful for removing curled hair follicles from a donor site comprises a generally tubular body disposed about a generally longitudinal axis and having a distal cutting end region terminating distally in a plurality of distally-extending circumferentially disposed, generally prong-like members carrying distally diverging cutting edges and separated by follicle-accommodating slits. In practice, the punch is oriented during the extraction process at the donor site so that the curled hair root passes into, and is spared from the advancing cutting edge by, a slit as the punch is inserted into and penetrates the tissue. The punch may then rotated slightly so that the cutting edges cut most of the tissue surrounding the follicle without making damaging contact with the follicle. It may be noted that a rotary motion may not be necessary and, if rotation is desired, it may be in one direction or be in the form of an (Continued)

oscillatory rotary movement, depending on characteristics of the donor site and targeted follicle.

14 Claims, 6 Drawing Sheets

(51) Int. Cl.
    *A61F 2/10*           (2006.01)
    *A61B 17/00*         (2006.01)
    *A61B 17/34*         (2006.01)
    *A61B 17/32*         (2006.01)

(52) U.S. Cl.
    CPC ..... *A61B 2017/320096* (2013.01); *A61F 2/10* (2013.01); *F04C 2270/0421* (2013.01)

(58) Field of Classification Search
    CPC ....... A61B 2017/320096; A61B 2017/320064; A61B 2017/3492; A61B 10/00; A61B 10/0266; A61B 10/0233; A61B 10/0275; A61B 2010/0208; A61B 2010/0225; A61B 2017/000969; A61F 2/10; A45D 26/00
    See application file for complete search history.

(56) References Cited

OTHER PUBLICATIONS

International Search Report and Written Opinion; PCT/US13/01991 (of which this is a "371" application).

\* cited by examiner

*fig. 12C*

FOLLICLE PUNCH FOR USE WITH CURLED FOLLICLES

FIELD OF THE INVENTION

This invention relates to surgical instruments and, more particularly, to a punch for extracting hair follicles from the skin.

BACKGROUND OF THE INVENTION

Hair transplantation is a surgical technique that involves moving skin containing hair follicles from one part of the body (the donor site) to bald or balding parts (the recipient site).

Hair naturally grows in follicles that contain groupings of 1 to 4 hairs, and transplant techniques typically move the 1-4 hair "follicular units" from the donor site to the recipient site.

The follicles of hair are typically removed from the donor site using punches of between 0.7 mm and 1.25 mm in diameter. The punches are tubular bodies having a skin-contacting cutting edge, and are typically mounted in a tool that causes the punch to rotate as the punch is brought into contact with the donor site. Hair follicles are very easily damage during the removal process, and damaged follicles are unlikely to be successfully transplanted.

Curled follicles are extremely susceptible to damage by follicle punches and are therefore particularly difficult to extract for successful transplantation. Such follicles are curled beneath the skin and are easily cut and/or damaged by the advancing cutting edge of conventional punches as the punch penetrates the donor site's tissue.

SUMMARY OF THE INVENTION

A punch that is particularly useful for removing curled hair follicles from a donor site comprises a generally tubular body disposed about a generally longitudinal axis and having a distal cutting end region terminating distally in a plurality of distally-extending circumferentially disposed, generally prong-like members carrying distally diverging cutting edges and separated by follicle-accommodating slits. In practice, the punch is oriented during the extraction process at the donor site so that the curled hair root passes into, and is spared from the advancing cutting edge by, a slit as the punch is inserted into and penetrates the tissue. The punch may then rotated slightly so that the cutting edges cut most of the tissue surrounding the follicle without making damaging contact with the follicle. It may be noted that a rotary motion may not be necessary and, if rotation is desired, it may be in one direction or be in the form of an oscillatory rotary movement, depending on characteristics of the donor site and targeted follicle.

The foregoing insertion process may be performed manually or under machine or computer control, and with or without the aid of an ultrasonic transducer coupled to punch to impart a vibratory cutting force against the tissue. In addition, a mechanism for automatically rotating the punch may be employed, and may accordingly be coupled to the ultrasonic transducer if one is used.

These and further details of the invention will be apparent to those of ordinary skill in the art from reading a description of the currently preferred embodiment of the invention described below, of which the drawing forms a part.

DETAILED DESCRIPTION OF THE PREFERRED EMBODIMENT

Referring to FIGS. 1-9, a preferred punch for extracting curled follicles is illustrated as comprising a generally tubular body 12 extending from a proximal end 14 to a skin-contacting distal end 16 about a generally central longitudinal axis 11. The currently preferred dimensions of the punch are displayed in the Figures in both inches (unbracketed) and millimeters (bracketed), said currently preferred dimensions being part of this Detailed Description.

The punch's generally tubular body 12 has a distal cutting end region terminating distally in a plurality of distally-extending circumferentially disposed, generally prong-like members 13 carrying distally diverging cutting edges 15 and separated by follicle-accommodating slits 22. The currently preferred number of members 13 is two because a pair of such members currently appears to provide the appropriate amount of cutting around the follicle together with sufficient slit width to safely accommodate entry and protection of the follicle during the extraction process.

As illustrated in the Figures, each of the preferred prong-like members 13 has a generally convex outer surface 18 and a generally concave inner surface 20 substantially the same as that of the tubular body. As also illustrated in the Figures, each of the prong-like members also has a beveled cutting surface 24, 26 terminating at a cutting edge 15, with the bevel preferably being on the inside of the punch so that it terminates at a cutting edge on the punch's outer diameter.

However, the formation of bevels on the outer surface of the punch is also possible, although not preferred, and is within the scope of the invention. It may be noted that it is currently believed that the cutting edge portion illustrated in FIG. 3 as 1.653 mm in length may be as long as approximately 4 mm or so, and that the follicle-accommodating slit 22 should preferably be approximately 2 mm-4 mm longer than the cutting edge portion.

The bevels 24, 26 are preferably created by grinding cutting edges outwardly from the interiors of the members 13 to produce sharp cutting edges. However, the bevels can also be formed by laser cutting, waterjet or abrasivejet cutting, chemical molding, and/or other manufacturing processes without departing from the scope of the invention.

The bevels 24, 26 preferably interface at an apex 25 of the prong-like member to provide a sharp, point-like, leading tip 27 which makes the initial penetration into the tissue that surrounds the targeted follicle, while the widening, generally semi-elliptical profiles of the prong-like members 13 cut more of the surrounding tissue as the punch is urged distally into the site. The leading tip can alternatively be a sharp rounded tip without departing from the scope of the invention.

The distal end region of the punch may be further provided with generally circumferentially-extending notch having a generally concave shape that generally circumscribes the punch's outer surface. The notch preferably extends 1-2 mm proximally from a location closely adjacent the tip of the punch. The generally concave shape serves two purposes. First, its preferred size and shape results in a wound with everted edges; as the punch enters the tissue surrounding the targeted follicle, the tissue outward of the cut expands against the concavity as it is passed by the cutting edge. When the punch is subsequently withdrawn, the tissue resumes its consequently everted shape. Second, the generally concave shape and preferred sharpening from the inside of the punch results in a cutting force that is outwardly directed away from the follicle and tissue to be extracted, deceasing the risk of damage to the follicle.

Alternatively, the punch can be provided with a flared distal end having a diameter that has a diverging inner diameter and diverging outer diameter along the last 1 mm or so, with the flared end region resulting in a preferred gap of approximately 1.25 mm between opposing tips. Gaps of great or lesser spacing may be utilized as well, depending on the subject's hair and follicle dimensions without departing from the scope of the invention.

Figure 1:
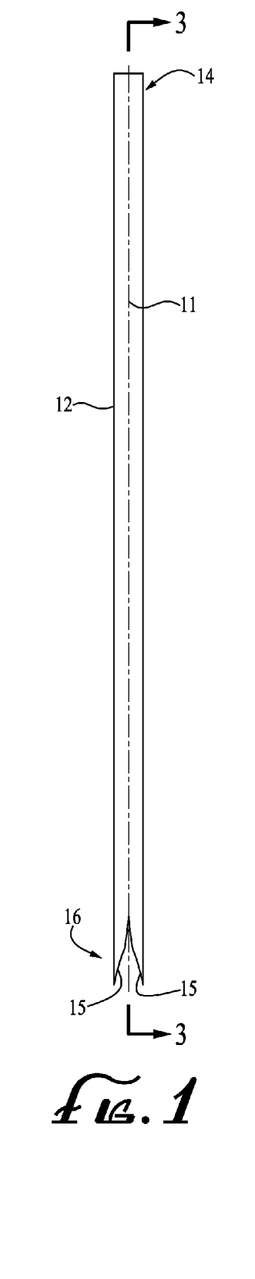
FIG. 1 is a front elevation view of a punch for removing hair follicles that is constructed in accordance with the invention.
Figures 2, 3:
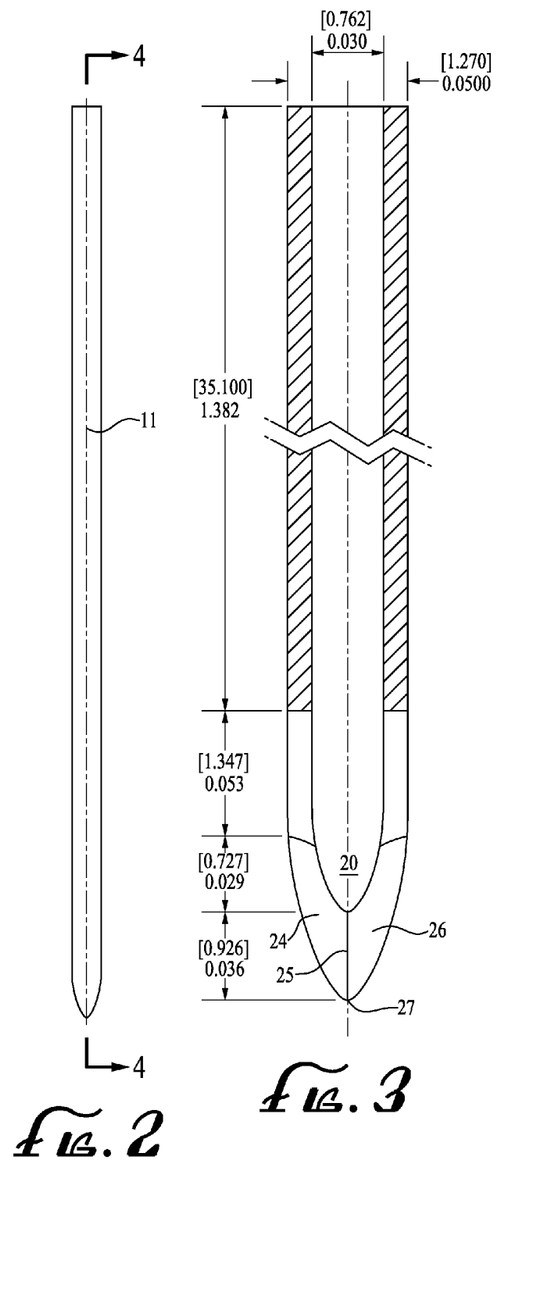
FIG. 2 is a side elevation view of a punch of FIG. 1.
FIG. 3 is a longitudinal section view of the punch of FIG. 1, taken along line 3-3 in FIG. 1.
Figure 4:
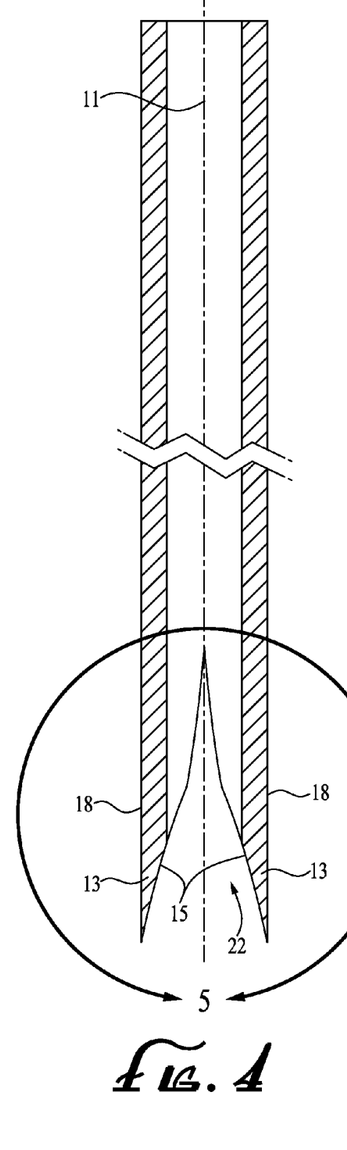
FIG. 4 is a longitudinal section view of the punch of FIG. 1, taken along line 4-4 in FIG. 2.
Figure 5:
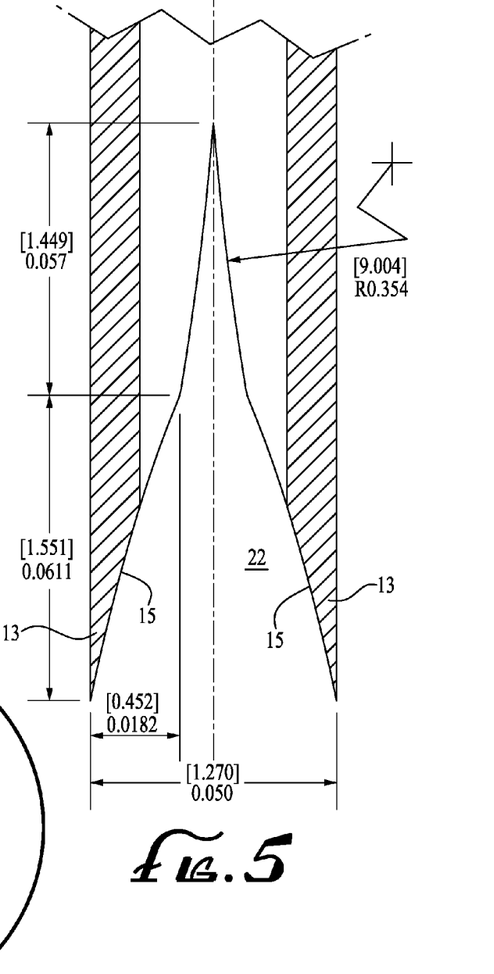
FIG. 5 is an enlarged fragmentary view of the portion of the punch illustrated within the line 5 of FIG. 4.
Figure 6:
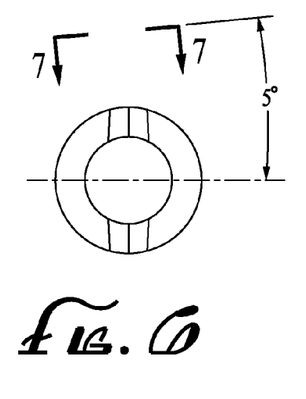
FIG. 6 is a bottom plan view of the punch of FIG. 2.
Figure 7:
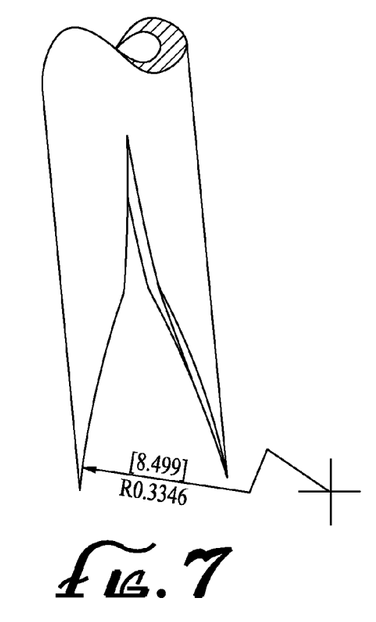
FIG. 7 is a fragmentary view in perspective of the cutting end region of the punch oriented per line 7-7 in FIG. 6 illustrated in FIG. 1.
Figure 8:
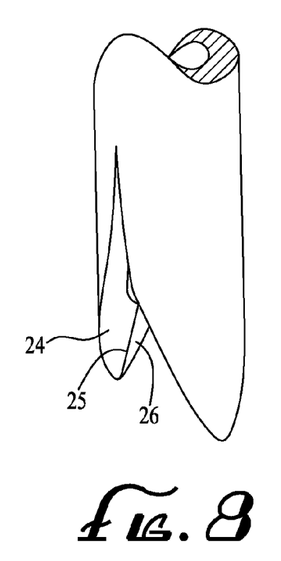
FIG. 8 is an oblique fragmentary elevation view of the cutting end region of the punch of FIG. 1.
Figure 9:
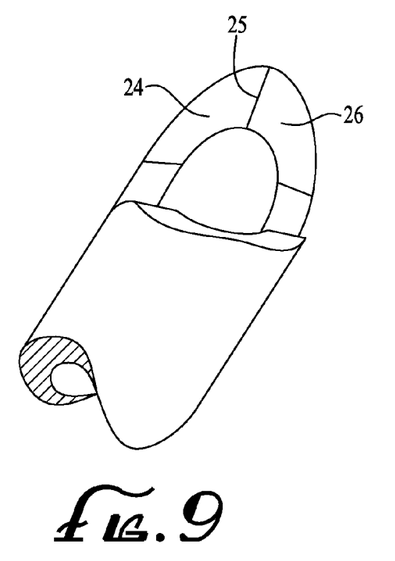
FIG. 9 is an oblique bottom view of the cutting end region of the punch of FIG. 1.

In one preferred configuration, the shape and dimensions of the slit 22 are, as best illustrated in FIGS. 4 and 5, a general inverted "V" profile having a relatively distal segment and a relatively proximal segment 22a that is more steeply tapered than the distal segment 22b. The more steeply tapered interior of the relatively proximal segment provides a slit length and width that accommodates the follicle as the punch penetrates the surrounding tissue, in order to spare the follicle from being cut; the less tapered distal segment of the slit results in adequate spacing of the cutting edges of adjacent prong-like members 13 from the follicle's root structure so that the cutting yields a viable implant. Although the same taper could be used for both segments, it is preferable not to do so since a generally uniformly steep taper (such as that of the preferred distal segment) would add unnecessary length to the punch to achieve the needed spacing between the prongs, while a generally uniformly shallow taper (such as that of the preferred distal segment) would fail to provide the slit length needed.

The cutting edge of the punch, which preferably extends from its leading tip to the beginning of the steeply tapered portion of the slit (i.e., the interface of the proximal and distal slit segments), may be smooth or include one or more serrations. If serrations are included, it is currently preferable that there be one or two serrations, with rounded edges, although the use of sharply angled edges would not depart from the scope of the invention.

Figure 10:
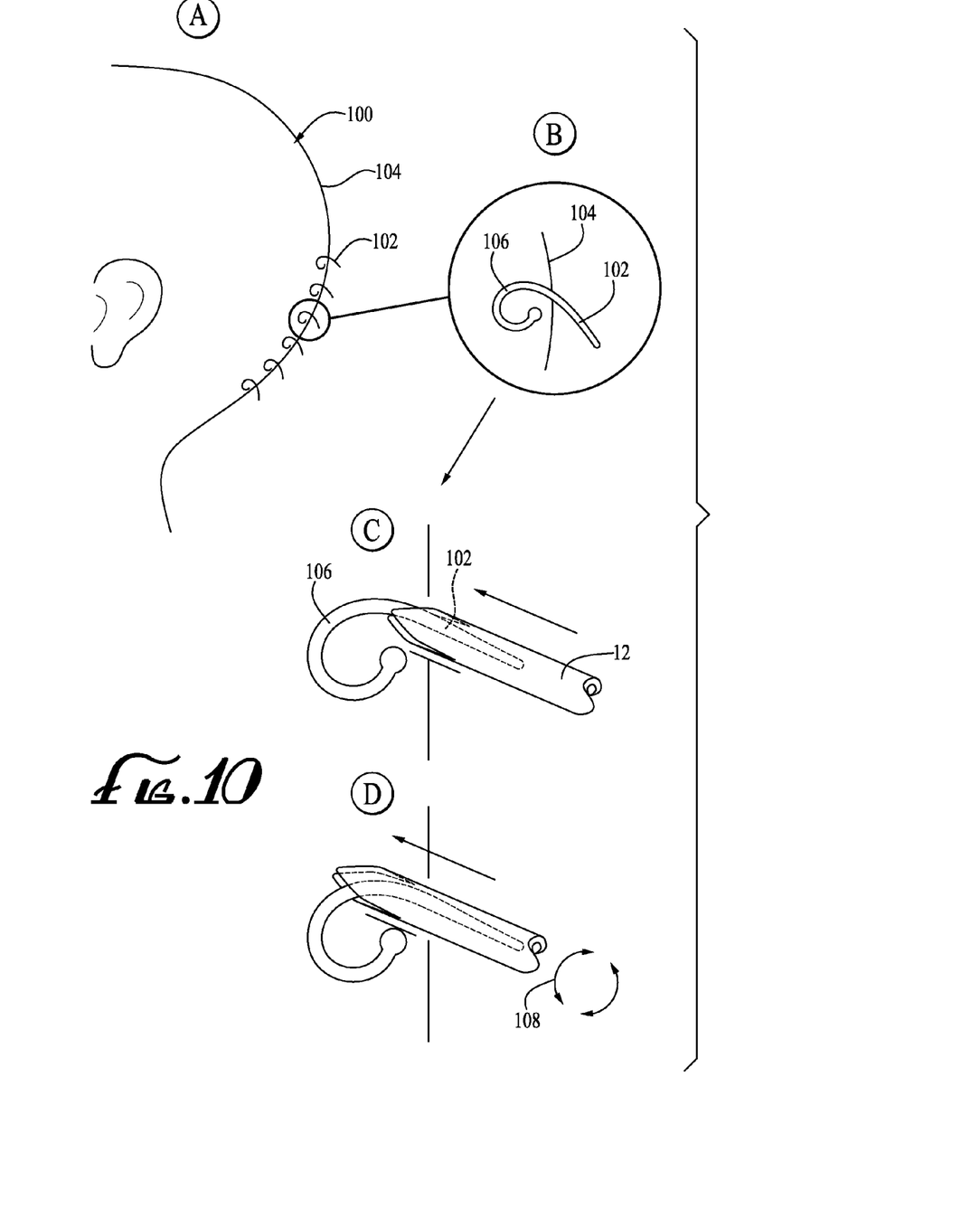
FIG. 10 is a schematic illustration of the preferred methodology for extracting a curled follicle in accordance with the invention.

FIG. 10 schematically illustrates (at "A") a subject's head 100 having a plurality of hairs 102 protruding from the skin 104. A hair 102 and its curled, subcutaneously-located follicle 106 is schematically illustrated in magnified form at "B".

As next schematically illustrated with greater magnification at "C", the preferred punch is inserted into the skin at the donor site in such a way that the hair enters the punch's interior while the follicle 106 passes uncut through the slit 22. As further illustrated at "D", the punch is advanced past the follicle, which remains undamaged by the cutting edges of the punch by passing through the slit. Once the punch has penetrated sufficiently, it can be partially rotated back and forth if desired, as schematically illustrated by the arrows, resulting in an arcuate cut in the tissue substantially circumscribing the curled follicle, while the follicle itself is spared by its clearance within the slit and isolation from the cutting edges. The intact hair follicle is then removed from the donor site for subsequent transfer to the recipient site.

To penetrate the skin, the punch could be manually pressed proximally by hand. Currently, it is believed that the use of an ultrasonic transducer to apply rapid, incremental, proximally-directed cutting force pulses to the tissue via the punch offers a more precisely controllable methodology for penetrating the tissue while the punch is positioned at the donor site and oriented so as to accommodate the follicle within the slit.

Figures 11A, 11B:
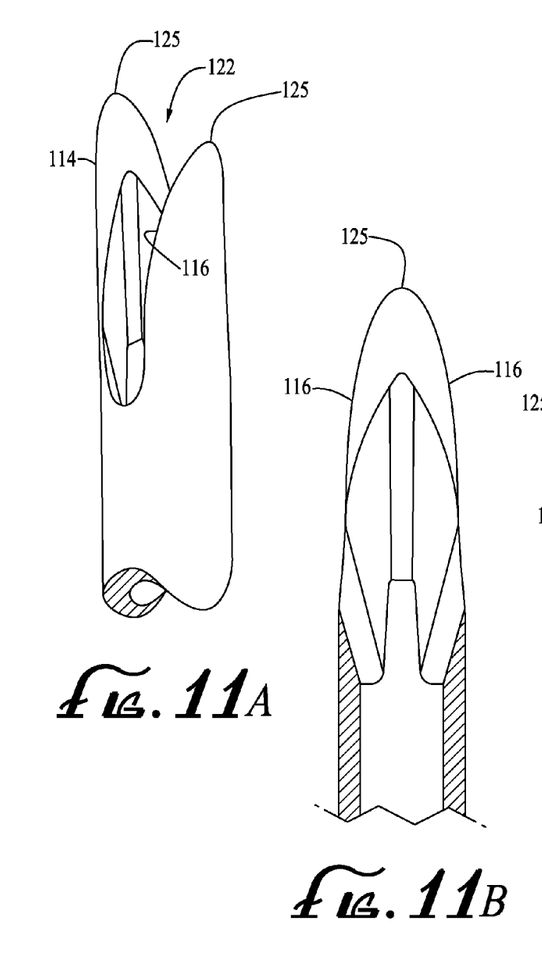
FIG. 11A is a right front oblique view, in schematic, of an alternative embodiment of a punch for removing hair follicles that is constructed in accordance with the invention.
FIG. 11B is a longitudinal sectional view of the punch of FIG. 11A, taken along line 11B-11B in FIG. 11C.
Figure 11C:
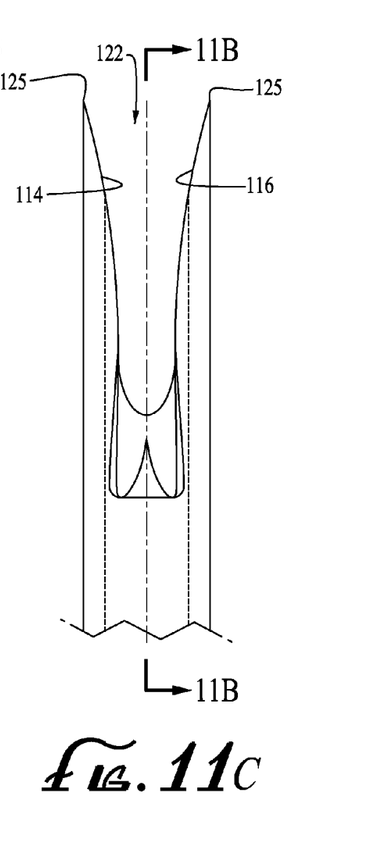
FIG. 11C is a front elevation view, in schematic, of the punch of FIG. 11A.

Turning to FIGS. 11A-C, a second currently preferred configuration of a follicle punch is illustrated with its currently preferred dimensions in mm). It should be noted that the interior surfaces of the punch are smooth; the apparent facets illustrated in FIGS. 11A and 11B are computer-generated "tangent" lines connoting a change in surface direction only.

The punch illustrated in FIGS. 11A-C comprises a pair of distally-extending circumferentially disposed, generally prong-like members 113 carrying distally diverging cutting edges 114, 116 and separated by a generally U-shaped follicle-accommodating slit 122. The cutting edge of each prong-like member is again preferably formed from the inside of the punch by grinding cutting edges outwardly from the interior region of the members. However, as noted earlier, the cutting edges can also be formed by laser cutting, waterjet or abrasivejet cutting, chemical molding, and/or other manufacturing processed without departing from the scope of the invention. The leading tips 125 of the punch illustrated in FIGS. 11A-C are sharp rounded tips that make the initial penetration into the skin and tissue surrounding the targeted follicle.

To minimize the risk of the follicle being cut during the extraction process, the formation of the cutting edges may be limited to the first 0.060 inches (1.52 mm) or so from the distal tip 125 of the punch, so that the cutting edges pass the follicle during insertion of the punch at the donor site and any subsequent contact between the punch and follicle is not with a cutting edge. The cutting edge may however extend the entire length, or a different length, of the slits.

The gap between the prong-like members of the punch illustrated in FIGS. 11A-C is preferably 0.02-0.03 inches (0.51-0.76 mm) wide. It preferably extends proximally from the distal tip of the punch for about 0.12 to 0.16 inches (3.05-4.06 mm).

Figures 12A, 12B, 12C:
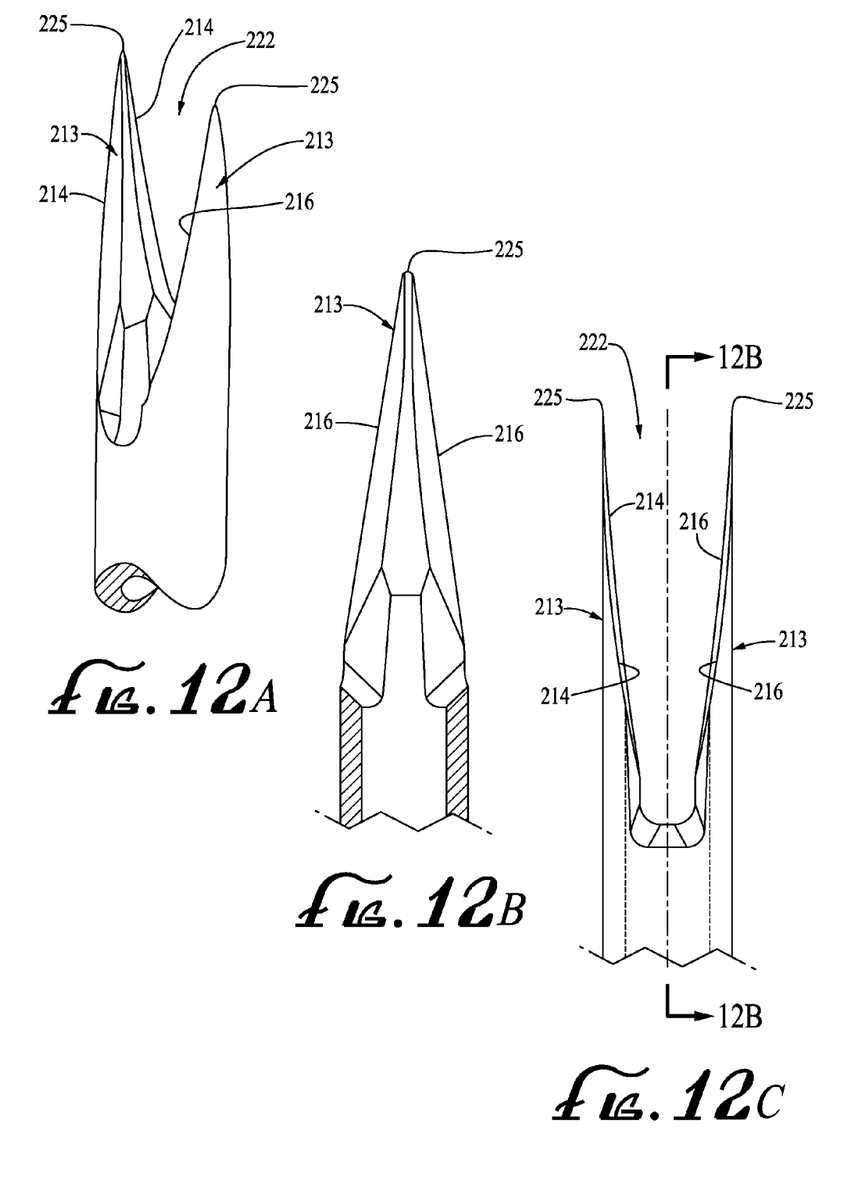
FIG. 12A is a right front oblique view, in schematic, of a second alternative embodiment of a punch for removing hair follicles that is constructed in accordance with the invention.
FIG. 12B is a longitudinal sectional view of the punch of FIG. 12A, taken along line 12B-12B in FIG. 12C.
FIG. 12C is a front elevation view, in schematic, of the punch of FIG. 12A.

Turning to FIG. 12A-C, another preferred variation of the punch is illustrated, wherein the punch comprises a pair of distally-extending circumferentially disposed generally prong-like members 213 that carry distally-diverging cutting edges 214, 216 separated by a generally U-shaped follicle-accommodating slit. The leading tips 225 of the members 213 are sharp pointed tips. Each cutting edge 214, 216 is preferably formed from the inside of the punch by grinding cutting edges outwardly from the interior region of the prong-like members. However, as noted earlier, the cutting edges can also be formed by laser cutting, waterjet or abrasivejet cutting, chemical molding, and/or other manufacturing processed without departing from the scope of the invention. To minimize the risk of the follicle being cut during the extraction process, the formation of the cutting edges may be limited to the first 0.060 inches (1.52 mm) or so from the distal tip of the punch, so that the cutting edges pass the follicle during insertion of the punch at the donor site and any subsequent contact between the punch and follicle is not with a cutting edge. The cutting edge may however extend the entire length, or a different length, of the gap.

The gap between the prong-like members of the punch illustrated in FIGS. 12A-C is preferably 0.03 inches (0.076 mm) wide, and preferably extends proximally from the distal tip of the punch for about 0.16 inches (4.06 mm).

As with FIGS. 11A-B, it should be noted that the interior surfaces of the punch illustrated in FIGS. 12A-B are smooth, and that the apparent facets are computer-generated "tangent" lines connoting a change in surface direction only.

Regardless of the specific version of follicle punch utilized, the inclusion of an ultrasonic transducer coupled to the punch and selectively operable to enhance the cutting operation is desirable. The transducer is mounted within a handpiece to which the punch is attached in a manner analogous to the transducer, handpiece and scaler tip of an ultrasonic dental scaler. The punch may be further mounted for reciprocating pivoting movement within the handpiece so as to move in such manner with or without ultrasonic vibratory movement. Likewise, the configuration may be such that ultrasonic vibratory movement can be generated with or without the pivoting movement.

In practice, it has been found that an adjustable degree of longitudinally reciprocating ultrasonic movement is desirable in that the appropriate degree of movement is a function of the subject's skin thickness and tissue, with higher settings being suitable when cutting through thicker skin or scar tissue for example. The use of the ultrasonic movement permits the surgeon or other operator of the equipment to better use his/her "fine motor" muscle movement to more precisely make the required incisions with greater sensitivity and finesse.

Although the present invention and its advantages have been described in detail, it should be understood that various changes, substitutions and alterations can be made herein without departing from the spirit and scope of the invention as will be defined by appended claims.

I claim:

1. A follicle punch, configured to remove a follicle with an initial penetration into skin comprising:
   a generally tubular body disposed about a longitudinal axis and having a distal cutting end region;
   the distal end region comprising a pair of distally-extending, circumferentially disposed, prong-like members carrying distally diverging cutting edges, the prong-like members separated by a pair of follicle-accommodating slits each having an inverted "V" profile, wherein the inverted "V" profile consists of a linearly tapered proximal segment and a tapered distal segment that is more steeply tapered than the proximal segment such that the tapered distal segment defines a wider opening than an opening defined by the tapered proximal segment;
   wherein the prong-like members are arranged to terminate distally into respective leading tips;
   wherein each leading tip is selected from one member of a leading tip set consisting of a V-shaped pointed tip and a U-shaped rounded tip; wherein the leading tip makes the initial penetration into tissue surrounding the follicle that make the initial penetration into tissue surrounding the follicle;
   wherein the follicle punch further includes:
      a handpiece coupled to the punch for enabling the punch to be controllably manipulated by a user in the removal of a hair follicle from a targeted donor site, and
      an ultrasonic transducer within the handpiece and coupled to the punch and selectively operable by the user to induce ultrasonic movement in the punch to enhance the cutting to controllably cut the skin and tissue around a targeted donor site.

2. The follicle punch of claim 1 wherein the follicle-accommodating slits extend proximally 1-2 mm from the tips of the prong-like members.

3. The follicle punch of claim 1 wherein the ultrasonic movement is generally axial.

4. The follicle punch of claim 1 wherein each of the prong-like members include a beveled cutting surface terminating at a cutting edge.

5. The follicle punch of claim 4 wherein a bevel is formed on an inside surface of the tubular body.

6. The follicle punch of claim 5 wherein the cutting edge formed by the beveled cutting surface is at an outer diameter of the follicle punch.

7. The follicle punch of claim 4 wherein a bevel is formed on an outside surface of the tubular body.

8. The follicle punch of claim 1 wherein the cutting edges having a longitudinal length consisting of a range between 1.65 mm and 4 mm.

9. The follicle punch of claim 8 wherein the follicle-accommodating slits are 2 mm to 4 mm longer than the cutting edges.

10. The follicle punch of claim 1 wherein the follicle-accommodating slits are 2 mm to 4 mm longer than a cutting edge of each prong-like member.

11. The follicle punch of claim 1 wherein a straight anterior cutting edge and a convex curved posterior cutting edge wherein the straight anterior cutting edge and the convex curved posterior cutting edge meet at a cutting tip.

12. The follicle punch of claim 1 wherein the prong-like members, which are arranged to terminate distally into the respective leading tips, are generally flared relative to the longitudinal axis of the generally tubular body.

13. The follicle punch of claim 1 wherein said one slit of the pair of slits extends further than an other slit of the pair of slits by a length in the range of 0.25 mm to 2 mm.

14. The follicle punch of claim 1 wherein the leading tip is sharp.

* * * * *